United States Patent
Stanjek et al.

(10) Patent No.: US 10,155,779 B2
(45) Date of Patent: Dec. 18, 2018

(54) PRODUCTION OF ISOCYANATE FUNCTIONAL ORGANOSILANES

(71) Applicant: Wacker Chemie AG, Munich (DE)

(72) Inventors: Volker Stanjek, Ampfing (DE); Lars Zander, Altoetting (DE)

(73) Assignee: WACKER CHEMIE AG, Munich (DE)

(*) Notice: Subject to any disclaimer, the term of this patent is extended or adjusted under 35 U.S.C. 154(b) by 0 days.

(21) Appl. No.: 15/526,518

(22) PCT Filed: Oct. 29, 2015

(86) PCT No.: PCT/EP2015/075139
§ 371 (c)(1),
(2) Date: May 12, 2017

(87) PCT Pub. No.: WO2016/078891
PCT Pub. Date: May 26, 2016

(65) Prior Publication Data
US 2017/0320896 A1   Nov. 9, 2017

(30) Foreign Application Priority Data
Nov. 21, 2014  (DE) .......................... 10 2014 223 823

(51) Int. Cl.
C07F 7/18   (2006.01)
B01J 31/02  (2006.01)

(52) U.S. Cl.
CPC ......... *C07F 7/1892* (2013.01); *B01J 31/0212* (2013.01)

(58) Field of Classification Search
CPC . C30B 7/14; C30B 29/12; C30B 29/60; C07F 7/24; H01L 51/0084
USPC ......................................................... 556/81
See application file for complete search history.

(56) References Cited

U.S. PATENT DOCUMENTS

| | | |
|---|---|---|
| 6,673,954 B1 | 1/2004 | Gedon et al. |
| 2007/0066784 A1 | 3/2007 | Radinger et al. |
| 2010/0069656 A1 | 3/2010 | Stanjek et al. |

FOREIGN PATENT DOCUMENTS

| | | |
|---|---|---|
| EP | 0 583 581 B1 | 2/1994 |
| EP | 0 649 850 B1 | 4/1995 |
| EP | 0 870 769 B1 | 10/1998 |
| EP | 1 692146 B1 | 8/2006 |
| EP | 1 937 697 B1 | 7/2008 |
| EP | 2 097 426 B1 | 9/2009 |
| JP | 2008001613 A * | 1/2008 |
| JP | 2008001613 A * | 1/2008 |
| WO | 2016/010900 A1 | 1/2016 |

OTHER PUBLICATIONS

Izumi et al., (JP 2008001613 A)—Machine Translation.*
CRC Handbook of Chem. & Phys. 71st ed., 1990-1991, 8-35-8-37.*
JP 2008001613 A—Machine Translation (Year: 2008).*
Christen, Hans-Rudolf, "Grundlagen der allgemeinen und anorganischen Chemie", Hans-Rudolf Christen, 9th edition, 1988, chapter 10.3.
Pietro Tundo, et. al., "Direct Synthesis of N-methylurthanes from primary amines with dimethyl carbonate", Pure and Applied Chemistry, (2005) vol. 77, pp. 1719-1725 (Jan. 1, 2005).

* cited by examiner

*Primary Examiner* — Clinton A Brooks
*Assistant Examiner* — Kofi Adzamli
(74) *Attorney, Agent, or Firm* — Brooks Kushman P.C.

(57) ABSTRACT

Isocyanate-functional silanes are prepared in high yield by pyrolysis of an O-carbamate prepared by reaction of a dialkylcarbonate with an aminoalkyl-functional silane in the presence of a basic catalyst, where the catalyst is neutralized by an acid which has a $pK_a$ of all protolysis stages of not more than 4. The neutralized or partially neutralized catalyst need not be removed prior to pyrolysis. The isocyanato-functional silanes exhibit higher storage stability as compared to those prepared from O-carbamates where catalyst neutralization is effected by weak acids.

13 Claims, No Drawings

PRODUCTION OF ISOCYANATE FUNCTIONAL ORGANOSILANES

CROSS REFERENCE TO RELATED APPLICATIONS

This application is the U.S. National Phase of PCT Appln. No. PCT/EP2015/075139 filed Oct. 29, 2015, which claims priority to German Application No. 10 2014 223 823.4 filed Nov. 21, 2014, the disclosures of which are incorporated in their entirety by reference herein.

BACKGROUND OF THE INVENTION

1. Field of the Invention

The invention relates to a process for preparing isocyanate-functional organosilanes.

2. Description of the Related Art

Various processes for preparing isocyanate-functional organosilanes, e.g. 3-isocyanatopropylsilanes of the formula (1), are known from the prior art. Suitable processes are described, inter alia, in EP 0 649 850 B1, EP 0 870 769 B1 or EP 2 097 426 B1.

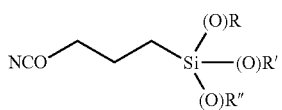

(1)

In all these processes, the isocyanate-functional organosilanes are prepared by thermolytic elimination of an alcohol from the corresponding carbamatoalkylsilanes, e.g. 3-carbamatopropylsilanes of the formula (2).

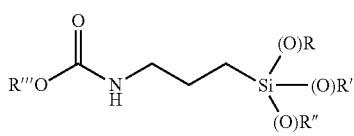

(2)

The carbamatoalkylsilanes are in turn usually prepared from aminoalkylsilanes, e.g. 3-aminopropylsilanes of the formula (3).

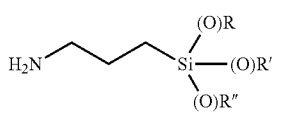

(3)

Here, the aminoalkylsilanes are reacted in the presence of a strongly basic catalyst, preferably using sodium alkoxides or potassium alkoxides, with dialkyl carbonates with elimination of an alcohol to give the respective carbamatoalkylsilanes. Such processes are described, for example, in EP 0 583 581, U.S. Pat. No. 6,673,954 or EP 1 937 697.

After the reaction is complete, the basic catalyst is usually neutralized, optionally with organic acids as recommended in EP 0 583 581 B1 or U.S. Pat. No. 6,673,954 B1, or according to the teaching of EP 1 937 697 B1 with ammonium halides, chlorosilanes or organic halogen compounds. The salts formed during the neutralization are preferably removed by filtration.

However, the processes as are to be found in the prior art have the critical disadvantage that the carbamatoalkylsilanes prepared by the abovementioned processes are unsuitable, or have only limited suitability, for being processed further by the above-described thermal elimination of an alcohol to form isocyanatoalkylsilanes without separate purification by distillation.

At the same time, carbamatoalkylsilanes are extremely difficult to distil since firstly they have a very low volatility and secondly they are only moderately thermally stable. Distillation is therefore possible only by means of a technically complicated distillation under an extremely good vacuum by means of a thin-film or short-path evaporator. It would therefore be desirable to be able to dispense with a separate purification of this product by distillation.

If carbamatosilanes prepared by processes corresponding to the prior art without separate purification by distillation are then used for preparing isocyanatosilanes, increased formation of low-volatility, sometimes even solid, by-products occurs. This can firstly correspondingly reduce the yield of the desired isocyanate-functional silanes and secondly also interfere in the preparative process, e.g. by formation of deposits in the corresponding reactor.

In particular, however, the isocyanate-functional silanes prepared in this way have a relatively low storage stability which is often only in the order of some days or at most a few weeks.

A process which no longer has these disadvantages would therefore be desirable.

SUMMARY OF THE INVENTION

The invention provides a process for preparing isocyanatoorganosilanes (IS) of the general formula (4)

from carbamatoorganosilanes (CS) of the general formula (5)

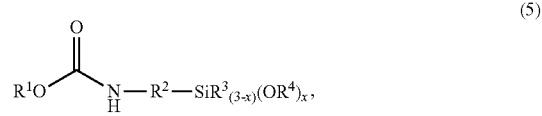

wherein carbamatoorganosilanes (CS) which have been prepared by reaction of at least one aminoorganosilane (AS) of the general formula (6),

with at least one dialkyl carbonate (DAC) of the general formula (7),

in the presence of a basic catalyst (K) having basic functions, where the basic catalyst (K) has been completely or partially neutralized with an acid (S) all of whose protolysis stages have $pK_a$ values of not more than 4.0 before preparation of the isocyanatoorganosilanes (IS),
where
$R^1$, $R^3$, $R^4$ and $R^5$ can be identical or different and are each a monovalent, unsubstituted or substituted hydrocarbon radical,
$R^2$ is a divalent, unsubstituted or substituted hydrocarbon radical and
x is 1, 2 or 3.

DETAILED DESCRIPTION OF THE PREFERRED EMBODIMENTS

The $pK_a$ value as a measure of the strength of an acid is known to a person skilled in the art; a suitable definition may be found in "Grundlagen der allgemeinen and anorganischen Chemie", Hans-Rudolf Christen, 9th edition, 1988, chapter 10.3.

If the acid (S) is an acid having only one acidic proton, it has only one protolysis stage which consequently has to have a $pK_a$ value of not more than 4.0.

If the acid (S) is an acid having more than one acidic proton, the above formulation according to which all the protolysis stages have $pK_a$ values of not more than 4.0 is to be interpreted as meaning that both the undeprotonated acid (S) and also all acids which can be derived from the undeprotonated acid (S) by single or optionally multiple deprotonation have to have $pK_a$ values of not more than 4.0.

The acid (S) preferably has $pK_a$ values of not more than 3.5 more preferably not more than 3.0, and in particular not more than 2.5, for all protolysis stages. What has been said in the two previous paragraphs also applies analogously to the smaller $pK_a$ values indicated here.

In the complete or partial neutralization, the acid (S) is added in such an amount that there are from 0.5 to 100 mol, preferably 0.8 to 10 mol, more preferably from 0.9 to 5 mol, and in particular from 0.99 to 2 mol, of acidic hydrogens per 1 mol of basic fractions in the catalyst (K).

Preferred acids (S) are accordingly strong inorganic acids. Particular preference is given to halogen-containing acids and acids containing halogen and oxygen, e.g. halogen-hydrogen acids having a direct halogen-oxygen bond, in particular hydrogen chloride and hydrochloric acid, sulfur-containing acids, in particular sulfuric acid and toluenesulfonic acid, nitrous acid and nitric acid. Preference is given to using concentrated acids, i.e. acids having a water content of <70% by weight, with acids having a water content of <10% by weight, in particular <5% by weight, being particularly preferred.

Preference is given to no further acids having greater $pK_a$ values being added in addition to the acids (S) having low $pK_a$ values according to the invention to the mixture of carbamatoorganosilanes (CS) and catalyst (K) before the preparation of the isocyanatoorganosilanes (IS).

Examples of radicals $R^1$ are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals; hexyl radicals such as the n-hexyl radical; heptyl radicals such as the n-heptyl radical; octyl radicals such as the n-octyl radical and isooctyl radicals such as the 2,2,4-trimethylpentyl radical; nonyl radicals such as the n-nonyl radical; decyl radicals such as the n-decyl radical; dodecyl radicals such as the n-dodecyl radical; octadecyl radicals such as the n-octadecyl radical; cycloalkyl radicals such as the cyclopentyl, cyclohexyl, cycloheptyl and methylcyclohexyl radicals; alkenyl radicals such as the vinyl, 1-propenyl and 2-propenyl radicals; aryl radicals such as the phenyl, naphthyl, anthryl and phenanthryl radicals; alkaryl radicals such as o-, m-, p-tolyl radicals, xylyl radicals and ethylphenyl radicals; and aralkyl radicals such as the benzyl radical, and the α- and the β-phenylethyl radicals.

Examples of substituted radicals $R^1$ are haloalkyl radicals such as the 3,3,3-trifluoro-n-propyl radical, the 2,2,2,2',2', 2'-hexafluoroisopropyl radical and the heptafluoroisopropyl radical, and haloaryl radicals such as the o-, m- and p-chlorophenyl radicals.

The radical $R^1$ is preferably an unsubstituted or halogen-substituted, monovalent hydrocarbon radical having from 1 to 6 carbon atoms, more preferably an alkyl radical having 1 or 4 carbon atoms, in particular the ethyl or methyl radical.

Examples of radicals $R^5$ are the radicals indicated for $R^1$. The radical $R^5$ is preferably an unsubstituted or halogen-substituted monovalent hydrocarbon radical having from 1 to 6 carbon atoms, more preferably an alkyl radical having 1 or 4 carbon atoms, and in particular an ethyl or methyl radical.

$R^1$ and $R^5$ are most preferably identical, with particular preference being given to both $R^1$ and $R^5$ each being ethyl radicals or methyl radicals.

Examples of radicals $R^4$ are, independently of one another, the radicals indicated for $R^1$.

The radicals $R^4$ are each preferably an unsubstituted or halogen-substituted, monovalent hydrocarbon radical having from 1 to 6 carbon atoms, more preferably an alkyl radical having from 1 to 4 carbon atoms, and in particular an ethyl or methyl radical.

All radicals $R^4$, $R^1$ and the radical $R^5$ are most preferably identical, with particular preference being given to all these radicals either each being ethyl radicals or else each being methyl radicals.

Examples of radicals $R^3$ are the radicals indicated for $R^1$. The radical $R^3$ is preferably an unsubstituted or halogen-substituted, monovalent hydrocarbon radical having from 1 to 6 carbon atoms, more preferably an alkyl radical having 1 or 4 carbon atoms, and in particular the methyl radical.

Examples of radicals $R^2$ are divalent alkylene radicals having from 1 to 20 carbon atoms, e.g. the methylene, ethylene, n-propylene, butylene, pentylene, hexylene, heptylene, octylene, nonylene or n-decylene radicals. The radicals mentioned can also have further alkyl substituents such as methyl, ethyl or propyl substituents. Halogen substituents, e.g. chlorine or bromine substituents, are also possible. In addition, the radicals $R^2$ can also be divalent cyclic radicals, e.g. cyclopentylene, cyclohexylene or phenyl radicals. These too can have the abovementioned alkyl or halogen substituents.

The radicals $R^2$ are preferably alkylene radicals having from 1 to 6 carbon atoms, more preferably a butylene, 2-methylpropylene, propylene and the methylene radical, in particular propylene and the methylene radicals.

The variable x preferably has the value 2 or 3.

The invention is based on a first surprising discovery that the mixtures of carbamatoorganosilanes (CS) and catalyst (K) which have been neutralized according to the invention with strong acids (S) can be used for preparing isocyanatoorganosilanes (IS) even without purification by distillation. In general, a removal of the neutralization product of the catalyst (K) and the acid (S) is not even necessary. The thermolytic elimination of alcohol not only proceeds significantly more unproblematically but also with significantly better yields than when the neutralization has been carried out using weaker acids which are not used according to the invention. This also applies to those cases in which the neutralization product of the catalyst (K) and the weaker acid which is not used according to the invention has been removed by filtration before the thermolytic elimination of alcohol.

Even more surprising is the second discovery on which this invention is based. Thus, the isocyanatoorganosilanes (IS) prepared by the process of the invention, i.e. using a strong acid (S) used according to the invention, display a dramatically improved storage stability.

The preparation of the carbamatoorganosilanes (CS) from aminoorganosilane (AS) and a dialkyl carbonate (DAC) in the presence of a basic catalyst (K) is preferably carried out at temperatures in the range from 0 to 120° C., more preferably in the temperature range from 35 to 90° C.

The components are preferably firstly combined at a lower temperature of from 40° C. to 70° C., preferably from 45° C. to 65° C., and stirring is carried out for a further 0.5 to 3 hours, after which the temperature is increased to temperatures of from 70 to 130° C., preferably in the range from 70 to 100° C., to complete the reaction. At this temperature, stirring is preferably carried out for a further 0.5 to 3 hours. Preferred examples of carbamatosilanes (CS) of the general formula (5) are N-(3-trimethoxysilylpropyl) O-methyl carbamate, N-(3-triethoxy-silylpropyl) O-ethyl carbamate, N-(3-methyldimethoxy-silylpropyl) O-methyl carbamate, N-(3-methyldiethoxy-silylpropyl) O-ethyl carbamate, N-(trimethoxysilylmethyl) O-methyl carbamate, N-(triethoxysilylmethyl) O-ethyl carbamate, N-(methyldimethoxysilylmethyl) O-methyl carbamate and N-(methyldiethoxysilylmethyl) O-ethyl carbamate, in particular N-(3-trimethoxysilylpropyl) O-methyl carbamate, N-(3-triethoxy-silylpropyl) O-ethyl carbamate, N-(trimethoxysilylmethyl) O-methyl carbamate, N-(triethoxysilylmethyl) O-ethyl carbamate and N-(methyldimethoxysilylmethyl) O-methyl carbamate.

These preferred carbamatosilanes (CS) are preferably prepared from aminosilanes (AS) of the general formula (6) and dialkyl carbonates (DAC) of the general formula (7) which have precisely the same radicals $R^1$ to $R^4$ and the same variable x than the carbamatosilane (CS) obtained. The radical $R^5$ in the dialkyl carbonate (DAC) preferably has the same meaning as the radical $R^1$.

In the reaction according to the invention, the aminosilanes (AS) and the dialkyl carbonates (DAC) are preferably used in a ratio of from 1.0:0.9 to 1.0:3.0, more preferably in a ratio of from 1.0:1.0 to 1.0:2.0, and in particular in a ratio of from 1.0:1.0 to 1.0:1.5. To achieve, firstly, a very complete conversion of the aminosilane component (AS) but, secondly, also attain a very good space-time yield, i.e. to use a very small excess of dialkyl carbonate (DAC), a ratio of aminosilane (AS) to dialkyl carbonate (DAC) of from 1:1.1 to 1:1.5 represents a particularly preferred embodiment.

Both the corresponding aminosilanes (AS) and the dialkyl carbonates (DAC) are commercially available from numerous different suppliers.

As catalyst (K), preference is given to use metal alkoxides, in particular alkali metal or alkaline earth metal alkoxides. Particularly preferred catalysts are sodium methoxide, sodium ethoxide, potassium methoxide, potassium ethoxide, calcium methoxide or calcium ethoxide. In a particularly preferred embodiment of the invention, an alkoxide whose alkyl group corresponds to the radicals $R^4$ in formula (3) is used. This is advantageous especially when all radicals $R^1$, $R^4$ and $R^5$ are identical.

The catalyst can be used neat or else in the form of a solution, in particular in the form of an alcoholic solution. In the case of an alcoholic solution, the alkyl groups of the alcohol and of the alkoxide are preferably identical. Suitable catalyst solutions comprising typically a 10-33% strength solution of the metal alkoxide in the corresponding alcohol are commercially available and are most preferably used because of their easy meterability.

The content of the catalyst (K) is preferably not more than 1.0% by weight, more preferably not more than 0.5% by weight, and in particular not more than 0.2% by weight, in each case based on the weight of the total reaction mixture.

The reaction mixture preferably contains, in addition to the components aminosilane (AS), dialkyl carbonate (DAC) and catalyst (K), further materials such as solvents in amounts of not more than 50% by weight, more preferably not more than 30% by weight, and in particular not more than 15% by weight, in each case based on the total reaction mixture. In a particularly preferred process variant, the reaction mixture contains no further components, in particular no further solvents, in addition to the reactants and the catalyst (K) and also any solvent in which the catalyst (K) was dissolved.

The neutralization of the catalyst (K) with the acid (S) used according to the invention can be carried out both at room temperature and at elevated temperatures. In a particularly preferred process, the neutralization is carried out immediately after the end of the reaction without the reaction mixture being heated or cooled appreciably, i.e. by more than 20° C. In an industrial process, this has the advantage that no additional times for heating and cooling procedures are required. The subsequent removal of the low boilers (see below) by distillation can also be commenced immediately afterward without appreciable heating or cooling steps, i.e. temperature changes of more than 20° C.

The usually solid neutralization product of the catalyst (K) and the acid (S) can optionally be removed by a filtration step. However, in a particularly preferred embodiment of the invention, this additional process step is omitted, i.e. the solid neutralization product of the catalyst (K) and the acid (S) is solid at 20° C. and is not separated off from the dialkyl carbonate (DAC) of the general formula (7).

The alcohol liberated in the preparation of the carbamatoorganosilane and also the dialkyl carbonate excess (DAC) optionally used are preferably removed by distillation. This can occur immediately after the reaction by the low boilers to be removed being distilled off directly from the reaction mixture, or else in a separate distillation step, e.g. using a thin-film or falling-film evaporator. The distillation can also be carried out in the presence of the neutralized but not yet removed catalyst (K).

However, preference is given to only the low-boiling components being removed by distillation from the carbamatoorganosilanes (CS) to be used according to the invention for the preparation of the isocyanatosilane. The carbamatoorganosilanes (CS) themselves, on the other hand, are not distilled.

The preparation of the carbamatoorganosilanes (CS) to be used according to the invention can be carried out both batchwise and continuously. This applies both to the actual reaction and to the work-up steps described. It is likewise conceivable for only individual process steps to be carried out continuously, e.g. for the reaction to be carried out continuously but the work-up to be carried out batchwise. Conversely, the reaction can of course also be carried out batchwise while subsequent work-up steps, in particular the removal of the low boilers by distillation, can be carried out continuously.

The carbamatoorganosilanes (CS) prepared according to the invention preferably have a purity of >90%, more preferably >95%, and in particular >97%.

The subsequent synthesis of the isocyanatoorganosilanes (IS) by thermolytic elimination of an alcohol from the carbamatoorganosilanes (CS) can be carried out in various ways. Preference is given to heating the carbamatoorganosilanes to preferably high temperatures of >200° C., more preferably >250° C., optionally even >280° C., with elimination of an alcohol molecule from the carbamate function occurring and the isocyanatoorganosilane (IS) being formed.

Here, the dissociation can naturally be carried out comparatively simply in a flask or vessel, with the more volatile reaction products being removed by distillation. However, more complicated processes as are described in EP 0 649 850 B1, EP 0 870 769 B1, EP 1 692 146 B1 or EP 2 097 426 B1 are usually more efficient.

Particular preference is given to processes as are described in EP 2 097 426 B1, in which the dissociation of the carbamatoorganosilanes is carried out continuously in a thin-film or short-path evaporator at a pressure of >100 mbar, preferably >500 mbar, in the presence of a catalyst (K'). This process has the advantage that the reaction products vaporize particularly quickly and therefore can undergo undesirable further reactions to only a small extent. In addition, the rapid vaporization brings about a continual shift in the reaction equilibrium in the direction of the products.

The catalyst (K') is preferably mixed into the carbamatoorganosilane (CS) before commencement of the reaction. The catalyst (K') is most preferably liquid, or else soluble in the carbamatoorganosilane (CS). Preferred catalysts (K') are all compounds which are used in polyurethane chemistry for catalyzing condensation reactions of isocyanates and alcohols. Mention may here be made by way of example of the organic tin compounds customarily used, e.g., dibutyltin dilaurate, dioctyltin dilaurate, dibutyltin diacetylacetonate, dibutyltin diacetate or dibutyltin dioctoate, etc. Divalent tin catalysts such as tin diacetate or tin dilaurate can likewise be used. Furthermore, it is also possible to use organic bismuth and/or zinc compounds, e.g. the various catalysts sold by Borcherts, e.g. Borchi-Kat 22, Borchi-Kat 24 or Borchi-Kat 0244, organic titanium compounds such as titanates, e.g. titanium(IV) isopropoxide or titanium(IV) acetylacetonate, organic iron compounds, e.g. iron(III) acetylacetonate, iron (II) acetylacetonate, or other metal compounds such as zirconium(IV) acetylacetonate, cobalt(III) acetylacetonate or manganese acetylacetonate.

Of course, combinations of a plurality of catalysts (K') can also be used. Preference is given to using catalysts which are nonvolatile or have a low volatility, in particular the above-mentioned metal complexes, with particular preference given to tin(IV), tin(II) and iron(III) complexes. The catalyst (K') is preferably used in concentrations of 1-10,000 ppm, with concentrations of 10-5000 ppm or 100-2000 ppm being particularly preferred.

In a preferred embodiment of the invention, an inert gas stream, e.g. a stream of argon, hydrogen or nitrogen, is passed through this evaporation unit during the vaporization procedure. This is preferably heated before introduction into the evaporation unit, in particular in an industrial process. Here, the hot carrier gas stream assists heating and vaporization of the reaction mixture. Nitrogen is preferred as gas.

The vaporized reaction products are then preferably fractionally condensed, with the alcohol eliminated preferably being separated off in gaseous form and the isocyanatoorganosilane (IS) and any carbamatoorganosilane (CS) partly vaporized being condensed together or optionally separately in succession. The removal of the alcohol prevents a back-reaction of the isocyanatoorganosilane (IS) formed. The removal of the alcohol preferably takes place in a condenser or a simple separation column in which the alcohol is taken off in gaseous form and silanes (IS) and (CS) are condensed out together.

The isocyanatoorganosilane (IS) is subsequently preferably purified by distillation, which can be carried out both continuously and batchwise, with the former being preferred. The carbamatoorganosilane (CS) separated off here is preferably recirculated into the thermolytic preparative process.

The process of the invention has the advantage that the isocyanatoorganosilanes (IS) obtained have an improved storage stability.

The process of the invention has the advantage that it gives very good yields and is thus inexpensive.

The process of the invention has the advantage that it generates by-products which can, for example, lead to malfunctions in the production process for example due to formation of deposits to only a small extent.

The process of the invention has the advantage that it is very simple and robust.

All symbols above in the above formulae each have their meanings independently of one another. In all formulae, the silicon atom is tetravalent.

In the following examples, all amounts and percentages indicated are, unless indicated otherwise, by weight, all pressures are 0.10 MPa (abs.) and all temperatures are 20° C.

Example 1a According to the Invention

Process for Preparing N-(3-trimethoxysilylpropyl) O-methyl Carbamate

A mixture of 1825.2 g (10.18 mol) of aminopropyltrimethoxy-silane and 12.6 g of a 30% strength by weight solution of sodium methoxide in methanol (corresponding to 3.8 g of pure sodium methoxide) is placed in a 4 l four-neck flask provided with dropping funnel, Liebig condenser, precision glass stirrer and thermometer, and heated to 55° C. At this temperature, 1100.4 g (12.22 mol) of dimethyl carbonate are introduced over a period of 60 minutes. In order to maintain the temperature, gentle cooling is necessary.

The mixture is subsequently stirred at 55° C. for another 1 hour and then heated to 80° C. This temperature is maintained for a further 2 hours.

Finally, 3.9 g of sulfuric acid (98% strength) are added. Only very slight clouding of the reaction mixture occurs here. A drop taken from the reaction mixture is placed on a previously moistened pH paper. The reaction mixture displays a pH of from 6 to 7.

The low boilers are removed by distillation from the neutralized reaction mixture. For this purpose, the pressure is reduced stepwise to 1 mbar, while the temperature at the bottom firstly remains at 80° C. and is finally increased once more to 110° C. The distillation is concluded as soon as no more distillate goes over. Analysis of the distillate by means of GC and/or $^1$H-NMR shows that the distillate consists virtually exclusively (i.e. to an extent of more than 99%) of the methanol liberated and the dimethyl carbonate used in excess.

A light-yellow product is obtained in a purity of 98.5%. The yield is virtually quantitative (>99%) based on the aminosilane used. Filtration to separate off the sodium sulfate formed is not necessary.

Example 2a According to the Invention

Process for Preparing N-(3-trimethoxysilylpropyl) O-methyl Carbamate According to the Invention The procedure of example 1a is repeated. However, 7.63 g of concentrated, i.e. 37% strength by weight, hydrochloric acid are added instead of the sulfuric acid to effect neutralization. As in example 1a, slight clouding of the reaction mixture also occurs here on addition of the acid.

Here too, filtration to separate off the sodium chloride formed is not necessary. The product purity is 97.3%.

Comparative Example 1a not According to the Invention

Process for Preparing N-(3-trimethoxysilylpropyl) O-methyl Carbamate which is not According to the Invention The procedure of example 1a is repeated. However, 4.66 g of acetic acid are added instead of the sulfuric acid to effect neutralization. Unlike example 1a, a readily filterable precipitate is formed on addition of the acid. The product purity is 98.3%.

After carrying out all the working steps described in example 1a, the batch is divided into two equal-sized halves. In the case of the first half, the precipitated sodium acetate is removed by means of an additional filtration step. The other half remains unfiltered.

Comparative Example 2a not According to the Invention

Process for Preparing N-(3-trimethoxysilylpropyl) O-methyl Carbamate which is not According to the Invention The procedure of example 1a is repeated. However, 4.55 g of citric acid are added instead of the sulfuric acid to effect neutralization. Like example 1a, only slight clouding of the reaction mixture occurs here on addition of the acid.

Removal of the solid by filtration by means of conventional paper filters is not possible. The product purity is 98.1%.

Comparative Example 3a not According to the Invention

Process for Preparing N-(3-trimethoxysilylpropyl) O-methyl Carbamate which is not According to the Invention The procedure of example 1a is repeated. However, 3.79 g of pure phosphoric acid are added instead of the sulfuric acid to effect neutralization. As in example 1a, only slight clouding of the reaction mixture occurs here on addition of the acid.

Removal of the solid by filtration by means of conventional paper filters is not possible. The product purity is 97.9%.

Example 1b

Process According to the Invention for Preparing 3-isocyanato-propyltrimethoxysilane The dissociation of the carbamatoorganosilane into isocyanatoorganosilane and alcohol is carried out in a thin-film evaporator having a length of 25 cm, an internal diameter of 8 cm and a wall temperature of 300° C.

300 g of the N-(3-trimethoxysilylpropyl) O-methyl carbamate prepared in example 1a are admixed with 0.21 g of dioctyltin dilaurate. The introduction is carried out at a rate of 110 ml/h at the upper end of the thin-film evaporator. A stream of nitrogen of 65 l/h is passed from the bottom upward, i.e. counter to the direction of travel of the reaction mixture.

Under these conditions, the outflow at the bottom is only about 10% of the amount of silane fed in.

The vaporized product mixture is passed together with the stream of nitrogen through a 10 cm long Vigreux column insulated by means of a vacuum jacket, with the liquid column runback being conveyed back into the thin-film evaporator. The temperature at the top of the Vigreux column is 158-164° C. The silane is condensed selectively from this gas stream by means of a conventional glass condenser at a temperature of 54° C. In a second condensation step, the methanol is then condensed out at a temperature of 0° C., before the stream of nitrogen is passed through a cold trap into the air extraction of the laboratory fume hood in which the entire plant is located.

231 g of condensed silane mixture are obtained. The colorless liquid is analyzed by means of $^1$H-NMR and gas chromatography. It contains 83.1% of 3-isocyanatopropyltrimethoxysilane, 16.4% of N-(3-trimethoxysilylpropyl) O-methyl carbamate and 0.1% of methanol.

In a subsequent fractional distillation, 172 g of 3-isocyanato-propyltrimethoxysilane are obtained in a purity of 98.9%.

Example 2b According to the Invention

Process According to the Invention for Preparing 3-isocyanato-propyltrimethoxysilane The procedure of example 1b is repeated. However, the product prepared in example 2a is used instead of the N-(3-trimethoxy-silylpropyl) O-methyl carbamate prepared in example 1a. All other reaction parameters remain unchanged.

225 g of condensed silane mixture are obtained. The colorless liquid is analyzed by gas chromatography. It contains 83.4% of 3-isocyanatopropyltrimethoxysilane, 16.2% of N-(3-trimethoxy-silylpropyl) O-methyl carbamate and 0.2% of methanol.

Comparative Example 1b

Process which is not According to the Invention for Preparing 3-isocyanatopropyltrimethoxysilane The procedure of example 1b is repeated. However, the unfiltered product prepared in comparative example 1a is used instead of the N-(3-trimethoxysilylpropyl) O-methyl carbamate prepared in example 1a. All other reaction parameters remain unchanged.

The isocyanatosilane preparation has to be stopped about 40 minutes after the commencement of the introduction of the silane/catalyst mixture because the thin film reactor becomes blocked as a result of solid deposits. Only a small amount of silane condensate is obtained, and this is not analyzed further.

Comparative Example 1c

Process which is not According to the Invention for Preparing 3-isocyanatopropyltrimethoxysilane The procedure of example 1b is repeated. However, the product prepared in comparative example 1a and subsequently filtered is used instead of the N-(3-trimethoxysilyl-propyl) O-methyl carbamate prepared in example 1a. All other reaction parameters remain unchanged.

The output at the bottom is increased appreciably, and only 180 g of condensed silane mixture are obtained. The colorless liquid is analyzed by gas chromatography. It contains 82.8% of 3-isocyanatopropyltrimethoxysilane, 16.2% of N-(3-trimethoxy-silylpropyl) O-methyl carbamate and 0.1% of methanol.

In a subsequent fractional distillation, 133 g of 3-isocyanato-propyltrimethoxysilane are obtained in a purity of 98.7%.

Comparative Example 2b

Process which is not According to the Invention for Preparing 3-isocyanatopropyltrimethoxysilane The procedure of example 1b is repeated. However, the product prepared in comparative example 2a is used instead of the N-(3-trimethoxysilylpropyl) O-methyl carbamate prepared in example 1a. All other reaction parameters remain unchanged.

The isocyanatosilane preparation has to be stopped about 30 minutes after commencement of the introduction of the silane/catalyst mixture because the thin film reactor becomes blocked as a result of solid deposits. Only a small amount of silane condensate is obtained, and this is not analyzed further.

Comparative Example 3b

Process which is not According to the Invention for Preparing 3-isocyanatopropyltrimethoxysilane The procedure of example 1b is repeated. However, the product prepared in comparative example 3a is used instead of the N-(3-trimethoxysilylpropyl) O-methyl carbamate prepared in example 1a. All other reaction parameters remain unchanged.

The isocyanatosilane preparation has to be stopped about 2 hours after commencement of the introduction of the silane/catalyst mixture because the thin film reactor becomes blocked as a result of solid deposits. About 100 g of silane condensate are obtained, and these are not analyzed further.

Example 1c

Stability Test on a 3-isocyanatopropyltrimethoxysilane Prepared by the Process of the Invention 100 g of the 3-isocyanatopropyltrimethoxysilane prepared in example 1b and purified by distillation are stored under protective gas in a glass flask for 3 months. The sample displays no optical change during this time.

After the end of the storage, the purity is determined again by means of GC. It has decreased from 98.9% to 96.5%.

Comparative Example 1d

Stability Test on a 3-isocyanatopropyltrimethoxysilane Prepared by a Process which is not According to the Invention 100 g of the 3-isocyanatopropyltrimethoxysilane prepared in comparative example 1c and purified by distillation are stored under protective gas in a glass flask for 3 months. The sample displays significant clouding during this time.

After the end of the storage, the purity is determined again by means of GC. It has decreased from 98.7% to 86.5%.

Example 3a According to the Invention

Process for preparing N-(methyldimethoxysilylmethyl) O-methyl Carbamate

A mixture of 360.3 g (3.97 mol) of dimethyl carbonate and 2.99 g of a 30% strength by weight solution of sodium methoxide in methanol (corresponding to 0.90 g of pure sodium methoxide) is placed in a 2 l four-neck flask provided with dropping funnel, Liebig condenser, precision glass stirrer and thermometer and heated to 55° C. At this temperature, 386.0 g (2.83 mol) of aminomethylmethyl-dimethoxysilane are introduced over a period of 60 minutes. In order to maintain the temperature, gentle cooling is necessary.

The mixture is subsequently stirred at 40° C. for another 1 hour and then heated to 80° C. This temperature is maintained for a further 1 hour.

Finally, 1.30 g of sulfuric acid (98% strength) are added. Only very slight clouding of the reaction mixture occurs here. A drop taken from the reaction mixture is placed on a previously moistened pH paper. The reaction mixture displays a pH of from 6 to 7.

The low boilers are removed by distillation from the neutralized reaction mixture. For this purpose, the pressure is reduced stepwise to 1 mbar, while the temperature at the bottom firstly remains at 80° C. and is finally increased once more to 110° C. The distillation is concluded as soon as no more distillate goes over. Analysis of the distillate by means of GC and/or $^1$H-NMR shows that the distillate consists virtually exclusively (i.e. to an extent of more than 99%) of the methanol liberated, the dimethyl carbonate used in excess and small amounts of methyltrimethoxysilane.

A light-yellow product is obtained in a purity of 96.8%. The yield is high (>95%) based on the aminosilane used. Filtration to separate off the sodium sulfate formed is not necessary.

Comparative Example 4a

Process for Preparing N-(methyldimethoxysilylmethyl) O-methyl Carbamate which is not According to the Invention The procedure of example 3a is repeated. However, 1.47 g of acetic acid are added instead of the sulfuric acid for neutralization. Unlike example 3a, a readily filterable precipitate is formed on addition of the acid. The product purity is 97.1%.

After carrying out all working steps described in example 3a, the precipitated sodium acetate is removed by means of an additional filtration step.

Example 3b

Process According to the Invention for Preparing α-isocyanato-methylmethyldimethoxysilane The procedure of example 1b is repeated. However, the N-(methyldimethoxysilylmethyl) O-methyl carbamate prepared in example 3a is used instead of the N-(3-trimethoxysilylpropyl) O-methyl carbamate prepared in example 1a. All other reaction parameters remain unchanged.

218 g of condensed silane mixture are obtained. The colorless liquid is analyzed by gas chromatography. It contains 60.4% of α-isocyanatomethylmethyldimethoxysilane, 39.2% of N-(methyldimethoxysilylmethyl) O-methyl carbamate and 0.2% of methanol.

Comparative Example 4b

Process which is not According to the Invention for Preparing α-isocyanatomethylmethyldimethoxysilane The procedure of example 3b is repeated. However, the product prepared in comparative example 4a is used instead of the N-(methyldimethoxysilylmethyl) O-methyl carbamate prepared in example 3a. All other reaction parameters remain unchanged.

The isocyanatosilane preparation has to be stopped about 60 minutes after commencement of introduction of the silane/catalyst mixture because the thin film reactor becomes blocked as a result of solid deposits. Only a small amount of silane condensate is obtained, and this is not analyzed further.

Comparative Example 4c

Process which is not According to the Invention for Preparing α-isocyanatomethylmethyldimethoxysilane The procedure of example 3b is repeated. However, a commercially available N-(methyldimethoxysilylmethyl) O-methyl carbamate (obtainable under the name GENIOSIL® XL 65 from Wacker Chemie AG, Munich, Germany) is used instead of the N-(methyldimethoxysilylmethyl) O-methyl carbamate prepared in example 3a. This commercially available carbamate is a product grade of N-(methyldimethoxysilylmethyl) O-methyl carbamate which has been purified by thin film distillation involving complicated apparatus after its synthesis, with all high-boiling impurities including all traces of salts having been removed.

220 g of condensed silane mixture are obtained. The colorless liquid is analyzed by gas chromatography. It contains 58.9% of α-isocyanatomethylmethyldimethoxysilane, 40.3% of N-(methyldimethoxysilylmethyl) O-methyl carbamate and 0.2% of methanol.

The invention claimed is:

1. A process for preparing isocyanatoorganosilanes of the formula (4)

comprising reacting at least one aminoorganosilane of the formula (6),

with at least one dialkyl carbonate of the formula (7),

to form carbamatoorganosilanes of the formula (5),

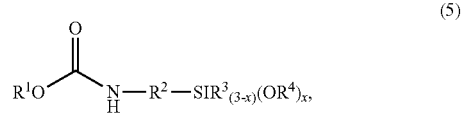

in the presence of a basic metal alkoxide catalyst, and
pyrolyzing the carbamatoorganosilanes of the formula (5)
   completely or partially neutralizing the basic metal alkoxide catalyst with an acid, all of whose protolysis stages have $pK_a$ values of not more than 4.0, before pyrolysis to form the isocyanatoorganosilanes,
where
$R^1$, $R^3$, $R^4$ and $R^5$ are identical or different and are each a monovalent, unsubstituted or substituted hydrocarbon radical,
$R^2$ is a divalent, unsubstituted or substituted hydrocarbon radical and
x is 1, 2 or 3.

2. The process of claim 1, wherein at least one acid is selected from the group consisting of halogen-containing acids and acids containing halogen and oxygen, sulfur-containing acids, nitrous acid and nitric acid.

3. The process of claim 1, wherein the acid is selected from among halogen-hydrogen acids having a direct halogen-oxygen bond.

4. The process of claim 2, wherein the acid is selected from among halogen-hydrogen acids having a direct halogen-oxygen bond.

5. The process of claim 1, wherein at least one acid is sulfuric acid or toluenesulfonic acid.

6. The process of claim 1, wherein the acid is added in the complete or partial neutralization in such an amount that from 0.9 to 5 mol of acidic hydrogens are present per 1 mol of alkoxide ions m the catalyst.

7. The process of claim 2, wherein the acid is added in the complete or partial neutralization in such an amount that from 0.9 to 5 mol of acidic hydrogens are present per 1 mol of alkoxide ions in the catalyst.

8. The process of claim 3, wherein the acid is added in the complete or partial neutralization in such an amount that from 0.9 to 5 mol of acidic hydrogens are present pet 1 mol of alkoxide ions in the catalyst.

9. The process of claim 1, wherein $R^1$ is an alkyl radical having 1 or 4 carbon atoms.

10. The process of claim 1, wherein $R^5$ is an alkyl radical having 1 or 4 carbon atoms.

11. The process of claim 1, wherein all radicals $R^4$, $R^1$ and $R^5$ are identical.

12. The process of claim 1, wherein the neutralization product of the catalyst and the acid is solid at 20° C. and is not separated off from the dialkyl carbonate of formula (7).

13. The process of claim 1, wherein the basic metal alkoxide catalyst comprises an alkoxide of an alkali metal or of an alkaline earth metal.

* * * * *

UNITED STATES PATENT AND TRADEMARK OFFICE
CERTIFICATE OF CORRECTION

PATENT NO.         : 10,155,779 B2
APPLICATION NO.    : 15/526518
DATED              : December 18, 2018
INVENTOR(S)        : Volker Stanjek et al.

Page 1 of 1

It is certified that error appears in the above-identified patent and that said Letters Patent is hereby corrected as shown below:

In the Claims

Column 14, Lines 60-61, Claim 6:
After "1 mol of alkoxide ions"
Delete "m" and
Insert -- in --.

Signed and Sealed this
Sixteenth Day of April, 2019

Andrei Iancu
*Director of the United States Patent and Trademark Office*